United States Patent [19]
Ferber et al.

[11] 3,992,153
[45] Nov. 16, 1976

[54] DOSIMETER FOR OXIDES OF NITROGEN

[75] Inventors: Benjamin I. Ferber; Fredrick A. Sharp; Robert W. Freedman, all of Pittsburgh, Pa.

[73] Assignee: The United States of America as represented by the Secretary of the Interior, Washington, D.C.

[22] Filed: May 20, 1976

[21] Appl. No.: 688,515

[52] U.S. Cl. ............................. 23/232 R; 23/254 R; 55/16, 23/253 TP
[51] Int. Cl.² ................... B01D 13/00; G01N 31/06
[58] Field of Search ........ 23/232 R, 254 R, 253 TP; 55/16, 158

[56] References Cited
UNITED STATES PATENTS

| | | | |
|---|---|---|---|
| 2,732,092 | 1/1956 | Lawrence | 55/158 |
| 2,966,235 | 12/1960 | Kammermeyer | 55/16 |
| 3,346,464 | 10/1967 | Ernst | 23/253 TP X |
| 3,545,931 | 12/1970 | McKinley, Jr. | 23/254 R X |
| 3,574,552 | 4/1971 | Rakowski | 23/253 TP |
| 3,681,027 | 8/1972 | Smith | 23/232 R |

*Primary Examiner*—Robert M. Reese
*Attorney, Agent, or Firm*—Thomas Zack; Gersten Sadowsky

[57] ABSTRACT

A dosimeter for the determination of integrated exposures to NO, $NO_2$ or exposures to both gases. The dosimeter provides for a convenient and accurate method for the determination of exposures which may be encountered by workers or miners in field environments.

28 Claims, 2 Drawing Figures

DOSIMETER FOR OXIDES OF NITROGEN

BACKGROUND OF THE INVENTION

1. Field of the Invention

This invention relates to the detection of oxides of nitrogen and instruments used to effect such determinations.

2. Description of the Prior Art

In various environments, nitrogen oxides ($NO_x$), i.e. NO and $NO_2$, may be present as the result of blasting or the operation of diesel engines. These gases can pose special problems in mines where the regulation of the atmosphere is not easily controlled. The current threshold limit value (TLV) for $NO_2$ is 5 parts per million (ppm) while that for NO is 25 ppm. The TLV is defined as the time-weighted average for exposure over a 40 hour work week. Thus, as established by the American Conference of Governmental Industrial Hygiensts in 1973, exposures to materials at levels above the TLV value are permissible for short periods if the time-weighted average is below the TLV value.

However, a ceiling (C) value has been established for $NO_2$ at 5 ppm whereby even short exposures to levels above the C value are not acceptable.

A small, pocket-type indicator for use in the field has been disclosed as described in U.S. Pat. No. 3,681,027. The indicator of this reference utilizes color changes in order to alert the wearer of unacceptable concentrations of $NO_2$ in the atmosphere. However, these indicators essentially only provide for instant determinations and are not acceptable in order to quantitatively assess the wearer's exposure over extended periods such that an accurate time-weighted average of the level of exposure can be established. Thus, these indicators would not find utilization in the determination of whether the wearer had been exposed to levels which were over the TLV value for $NO_2$. Additionally, although exposures to $NO_2$ are generally more of a problem than exposure to NO in view of the lower TLV of $NO_2$ as well as the fact that $NO_2$ has a ceiling value, determination of the level of exposure to NO can be desirable but is not provided by the indicators of U.S. Pat. No. 3,681,027.

A further example of a dosimeter for the detection of $NO_2$ is disclosed in U.S. Pat. No. 3,574,552. However, the dosimeter strips which are prepared according to this reference also depend on the occurrence of color changes to determine the exposure levels. Thus, the ability of a wearer to determine the exposure level would depend on the wearer's ability to correlate the color produced by the dosimeter strip with colors produced by exposure to known levels. Additionally, such dosimeter strips would not be particularly useful in the accurate determination of the time-weighted integrated exposure of the wearer. This would result in an inability to accurately determine whether the wearer had been exposed to levels of the $NO_2$ gas above the TLV value. Further, U.S. Pat. No. 3,574,552 does not provide for the determination of exposure to NO gas.

The use of detector tubes for the determination of levels of various gases is also known as described in U.S. Pat. No. 3,068,073 which describes a detector tube for the determination of carbon dioxide gas. In the use of detector tubes, a material is provided which changes color on exposure to a particular gas, in a transparent tube which is sealed at both ends prior to the determination of the level of the gas present. When the determination of the level present is required, the seals are broken and a known volume of gas is pumped through the tube and any color change as well as the length of such color in the tube is noted. However, the testing must be done at the site in question and, therefore, the presence of a pump may prove cumbersome and undesirable. Additionally, such methods cannot provide integrated time-weighted exposures and are dependent upon the ability of the operator to accurately distinguish changes in color. Further, the accuracy of such stainlength detector tubes is limited and can give a reading 25 to 50% above or below the actual level present.

Instrumental methods which utilize chemiluminescent or electrochemical methods are known but require the utilization of expensive, fragile and bulky instruments. Further, such methods require pumps with accompanying batteries and/or line current. Such instruments can utilize sophisticated electronic circuits which may require servicing and maintenance. Further, instruments of this type may require user manipulation for calibration and adjustment which is inconvenient in many applications for on-site determinations.

Finally, the phenoldisulfonic acid method is known for the determination of total oxides of nitrogen. However, such a determination has a disadvantage in that NO cannot be distinguished from $NO_2$. Since $NO_2$ has a significantly lower TLV than NO as well as a ceiling value, this method may not prove to be adequate in various applications. This method is described in "Determination of the Oxides of Nitrogen by the Phenoldisulfonic Acid Method" by Beatty et al., Bureau of Mines Report of Investigations 3687 (February, 1943) and in "Rapid Determination of Nitrogen Oxides with Use of Phenoldisulfonic Acid", by Coulehan et al., *Environmental Science and Technology*, Volume 5, No. 2, page 163 (February, 1971). This method requires a fragile glass bottle for sample collection and the analysis is lengthy and involved, requiring a chemist or highly-trained technician to operate elaborate equipment.

SUMMARY OF THE INVENTION

The present invention provides a light-weight and convenient dosimeter which can be worn by a wearer whereby integrated time-weighted exposures to $NO_2$ can be determined. By a simple modification, the determination of exposure to $NO_x$ can also be determined. Further, by the use of two dosimeters, one with and one without the modification, the determination of levels of exposure to NO can be determined.

The principle involved in the dosimeter of the present invention comprises the permeation of $NO_2$ through a membrane after which it is converted to $NO_3^-$ ion by the action of an oxidation agent. After exposure, the level of $NO_3^-$ ion is determined by correlation to levels of $NO_3^-$ ion that are present in dosimeters exposed to known concentrations of NO, $NO_2$ or $NO_x$. The accuracy of exposure levels as determined by the dosimeters of the present invention have been found to be highly accurate and, thus, the invention provides a useful method for the determination of integrated time-weighted exposures which can be used to determine whether the TLV has been exceeded during the exposure.

The present invention was summarized in the American Industrial Hygiene Association Journal, Vol. 37, No. 1, January 1976 at pages 32–36.

DETAILED DESCRIPTION OF THE INVENTION

Figures 1, 2:
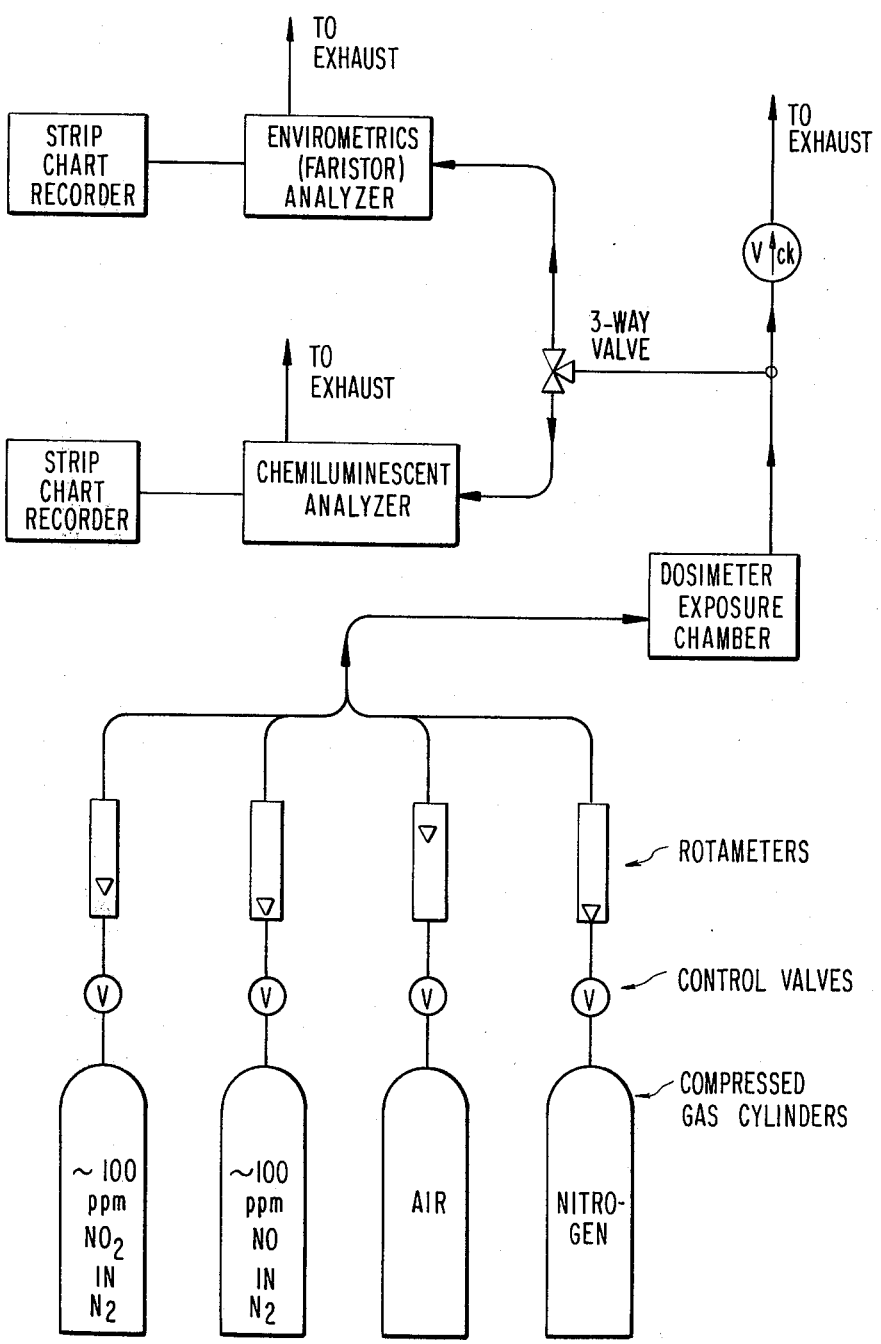
FIG. 1 indicates a side view of a dosimeter according to the present invention, the aqueous solution for the conversion of $NO_2$ to $NO_3^-$ being present in the cavity 5 and separated from the atmosphere by means of the membrane 4.
FIG. 2 is a flow diagram of the testing procedure for the exposure of a dosimeter according to the present invention to known concentrations of NO, $NO_2$ or $NO_x$ gases.

The dosimeter can be constructed from a container of any convenient size or weight. Thus, the dosimeter indicated in FIG. 1 is constructed from a threaded Teflon cup 3 and a threaded brass cover 1. However, any materials which are substantially inert to NO and $NO_2$ as well as the materials contained in the aqueous solution which is placed in cavity 5 can be used. Thus, polystyrene Petri dishes have been found to be usable in the dosimeters of the present invention.

The membrane is shown at 4 in FIG. 1 and can essentially be any membrane which is substantially permeable only to gases. Preferred membranes are dimethyl silicone membranes such as the Perm-selective membranes which can be obtained from General Electric and as described in "General Electric Perm-selective Membrane", Bulletin GEA-868A, General Electric Company (Medical Development Operation, Chemical and Medical Division), Schenectady, New York (1970). Further, such dimethyl silicone Perm-selective membranes are preferably unbacked, i.e. are not laminates which contain strengthening layers. It has been found that such membranes can be reused in the dosimeters of the present invention and continue to provide accurate results. Preferably, the membrane is a dimethyl silicone disc having an outside diameter of about 56 millimeters and a thickness of about 0.025 millimeters (about 1 mil). If a somewhat thicker membrane of the same material were utilized, less $NO_2$ gas would permeate the membrane and thus, less $NO_3^-$ ion would be formed in the aqueous solution contained in cavity 5 in FIG. 1. Therefore, such a thicker membrane would result in a somewhat lower ratio of $NO_3^-$ ion formed to the concentration of $NO_2$ gas in the atmosphere. This would result in the fact that the levels of $NO_3^-$ ion found in dosimeters in the field would be compared against a different set of standards than those found with the utilization of the thinner membrane. However, this is not a significant problem since the dosimeters are usually standardized at regular intervals in any case.

The aqueous solution which provides the conversion of the $NO_2$ gas which has permeated the membrane to $NO_3^-$ ion can be contained in the dosimeter as shown in FIG. 1 in cavity 5. The aqueous solution is about 0.0005 molar in sulfuric acid. Concentrations of sulfuric acid up to about 0.2 molar have been utilized but the about 0.005 molar figure has been found to be preferred. Further, the aqueous solution contains an oxidation agent which can effect the conversion of $NO_2$ to $NO_3^-$ ion. The preferred agent is hydrogen peroxide which can be present in the optimal concentration of about 0.004 molar. Concentrations lower than this figure have been utilized, e.g. concentrations of 0.0004 and 0.0002 molar, while higher concentrations can result in an excess amount of hydrogen peroxide which must be removed before the determination of the concentration of $NO_3^-$ ion. Thus, the preferred aqueous absorbing solution is about 0.0005 molar in sulfuric acid and about 0.004 molar in hydrogen peroxide. As explained below, the water used in the aqueous solution should be as pure as possible in order to eliminate the possibility of the presence of ions which can affect the readings obtained. However, this is not a substantial problem and can readily be effectively eliminated.

The aqueous absorbing solution which is present in the dosimeter, e.g. in cavity 5 in FIG. 1, can be in any amount which indicates results of the desired accuracy but must completely fill the cavity. That is, since the amount of $NO_2$ which is absorbed by the dosimeter is proportional to the size of the membrane, the membrane should cover as large an area as possible but should be limited according to the utility of the dosimeter as a portable and convenient dosimeter which does not interfere with the wearer. Excellent results have been obtained with dosimeters produced according to the present invention having an outside diameter of about 6.3 centimeters in that the dosimeters are small, convenient and provide accurate results. For a dosimeter of this size, it has been found that the use of about 4 milliliters of absorbing solution is optimal in that as the volume of solution is increased in a dosimeter having a given membrane size, the concentration of $NO_3^-$ ion which is produced in the solution after exposure tends to decrease. Smaller concentrations of $NO_3^-$ ion can result in difficulty in the accurate determination of the precise concentration, and thus, the accurate determination of the concentration of $NO_2$ to which the dosimeter was exposed. Further, as explained below, the present technology for the determination of $NO_3^-$ ion concentration limits the volume of sample to volumes of about 2 milliliters or more. In view of these considerations, i.e. the size of a convenient dosimeter limits the maximum volume while the determination of $NO_3^-$ ion concentration at the present time limits the minimum volume, it has been found that optimal results in view of all considerations can be obtained when about 4 milliliters of aqueous absorbing solution are used in the dosimeter of the present invention. However, it should be recognized that this figure is not arrived at through any inherent limitations on the invention itself but, rather, comes about through merely physical considerations which are made at the present time.

In the dosimeter of the present invention, the membrane can be exposed to the atmosphere through a hole in the dosimeter or through several holes whereby outside contact with the membrane itself is avoided, e.g. by insertion of a small object such as a pencil through the larger hole.

In the embodiment of the invention shown in FIG. 1, the dosimeter comprises a threaded cup 3 which contains a cavity 5 into which the absorbing solution is placed. Thereafter, the membrane 4 is placed over the cavity 5 and secured by means or an O-ring 2, the pressure being applied by means of a cover ring 1 which is screwed into place. The dosimeter is then ready for either testing to establish the standard by which the dosimeters used in the field will be measured or is ready for actual exposure in the field.

The dosimeter may have an attaching means such as a clip 7 as shown in FIG. 1 for convenient use in the field.

In a further embodiment of the present invention, a dosimeter is provided which contains means for the conversion of NO to $NO_2$ whereby a determination of the exposure of $NO_x$ can be obtained. This conversion means should be situated in the dosimeter on the side of the membrane opposite to the side containing the aqueous absorbing solution which converts the $NO_2$ gas to the $NO_3^-$ ion. It must be seen that the present invention provides a method for the determination of exposure to NO gas by the provision of two dosimeters during the exposure, one with and one without the NO to $NO_2$ conversion means.

A preferred NO to $NO_2$ conversion means is an oxidation filter made by impregnating a glass-fiber filter with acidic sodium dichromate. An example of such a filter is the Reeve Angel No. 934-AH glass filter having a 7-centimeter diameter. The acidic sodium dichromate solution can be prepared by dissolving about 2.5 grams of sodium dichromate in 100 milliliters of about 2.5% sulfuric acid. Oxidation filters prepared in this manner can be stored by arrangement in a stack in a closed glass container. When utilized in the dosimeters shown in FIG. 1, the oxidation filter is placed on top of the O-ring prior to the tightening of the cover ring.

A suitable conversion means is the filter 6 shown in FIG. 1.

Utilization of two such oxidation filters in the dosimeters shown in FIG. 1 was found to be unnecessary since the results obtained during exposure to NO gas were found to be similar. Further, utilization of more concentrated sodium dichromate solution was also found to be unnecessary.

Dosimeters according to the present invention were found to be stable for extended periods of time and when individually capped, the dosimeters proved stable for periods of at least one month.

It has been found that the dosimeters of the present invention can be used over a wide range of exposure temperatures. Preferably, exposure temperatures of 15° to 50° C should be used, more preferably 20° to 40° C. Use in these temperature ranges can provide determinations in applications such as coal or metal mines wherein the dosimeters of the present invention would probably find their greatest utility. However, the dosimeters of the present invention would find utility in other applications wherein exposure to NO, $NO_2$ or $NO_x$ is probable. In this connection, it should be noted that the exhaust from diesel engines contains high amounts of NO gas. However, NO gas is rapidly oxidized by the oxygen in air to $NO_2$. Exhausts from blasting operations contain higher amounts of $NO_2$ relative to NO gas.

Since the membranes utilized in the dosimeters of the present invention are permeable to substantially all gases, interferences with the measurement of $NO_3^-$ ion may occur caused by the presence of other ions. Such interferences are described in the instruction manual for the Nitrate Ion Electrode, Model 92–07 manufactured by Orion Research, Incorporated, of Cambridge, Mass. Polar gases such as $NO_2$, $H_2S$, $CO_2$ and $SO_2$ permeate such membranes more rapidly than NO, CO, $N_2$ and $O_2$. Since sulphate ion interferes only slightly with the determination of $NO_3^-$ ion, sulfuric acid is utilized in the aqueous absorbing solution of the present invention. Since hydrogen ions interfere strongly with the determination, relatively low concentrations of sulfuric acid are used. Since chloride ion tends to strongly interfere in the determination and since this ion can be present in sources of the water utilized as well as in the atmosphere in the form of hydrogen chloride gas, it might be found that removal of the chloride ion is necessary before determination of the $NO_3^-$ concentration.

Thus, it has been found that chloride ion is substantially the only moiety that interferes to a significant extent with the determination of $NO_3^-$ ion concentration. However, the interference can be eliminated by adding a silver-impregnated ion-exchange resin to the exposed aqueous absorbing solution prior to the $NO_3^-$ ion concentration. The silver-impregnated ion-exchange resin can be prepared by the treatment of an ion-exchange resin such as Dowex 50WX8 ion-exchange resin which is strongly acidic (Grade p.A., 50–100 mesh obtained from Dow Chemical) with a silver nitrate solution. The thus-impregnated resin is then washed with water to remove excess silver nitrate and dried. When about 4 milliliters of the aqueous absorbing solution is utilized in the dosimeter, the effect of the chloride ion present can be substantially eliminated by the addition of about 0.1 cubic centimeters of the thus-prepared resin to the sample in order to precipitate silver chloride from the solution. When this is done, the voltage readings obtained from the solution will increase as the silver chloride is precipitated and when a stable reading is obtained, it can be assumed that the chloride ion present has been substantially eliminated. However, it can be seen that a great variety of methods for the removal of chloride ion can be used in the present invention if such chloride ion is present to a significant extent.

In the method for the determination of exposure to NO, $NO_2$ or $NO_x$ of the present invention, dosimeters are prepared by utilizing one aqueous absorbing solution. Exposure of sample dosimeters to known quantities of NO, $NO_2$ or $NO_x$ is then effected by means of an apparatus such as that shown in FIG. 2. A dosimeter is placed in the dosimeter exposure chamber and the contaminant gas mixture is introduced into the test chamber, e.g. at a flow rate of 1200 milliliters per minute. The effluent from the test chamber is vented to a fume hood with a portion of the exhaust being split to the monitoring analyzers for the determination of the gas in question in the atmosphere to which the dosimeter has been exposed. Flow rates of 1000 to 13,000 milliliters per minute have been utilized at atmospheric pressure without significant differences in the results obtained.

The chemiluminescence analyzer as shown in FIG. 2 is, for example, a Scott Model 125 NO/$NO_x$ Chemiluminescence Analyzer obtained from Scott Environmental Technology, Inc. of Plumsteadville, Pa.

similar results were obtained by the use of an EnviroMetrics Nitrogen Oxide Analyzer, Model N-322C from International Biophysics Corporation of Irvine, Ca.

The time weighted integrated exposure of the test dosimeter can be found by the multiplication of each exposure figure by the time of said exposure followed by the addition of these figures and, finally, the division of the total by the total exposure time.

After the determination of the gas exposure of each of the test samples, the $NO_3^-$ concentrations were then determined. The 4 milliliter solution could either be transferred to a 50 milliliter beaker for testing or could be tested directly in the dosimeter. Before testing, a material for the removal of chloride ion can be added as explained above. Preferably, the samples should be stirred during testing.

Preferably, a nitrate ion electrode and double junction reference electrode are used for determining aqueous $NO_3^-$ ion concentrations. However, any method for the accurate determination of such concentrations can be used. Nitrate ion electrodes that can be used are those such as the Orion Model 92–07 or 93–07 obtained from Orion Research, Inc. of Cambridge, Massachusetts. Alternatively, other nitrate ion electrodes can be obtained from Beckman Instruments, Inc. of Fullerton, Ca., e.g. No. 39618 or those obtained from Corning Glass Works of Corning, New York, eg. Model No. 476210.

Millivolt measurements can be made with an instrument such as a Fisher Model 320 Accumet Expanded Scale pH Meter.

Before testing of the test dosimeters, the electrode system is standarized by measurement of various concentrations of $NO_3^-$ ion concentrations, e.g. 1, 5, 10, 50 and 100 ppm of $NO_3^-$, W/V (micrograms of $NO_3^-$/milliliters of solution). The millivolt readings from these standard $NO_3^-$ ion test samples are then plotted on a linear ordinate scale versus parts per million of $NO_3^-$ on a logarithmic scale on the abscissa. From this test chart, the millivolt readings which are obtained from the dosimeters can be correlated to parts per million $NO_3^-$ ions quickly and accurately. Preferably, a new test chart should be made up at regular intervals.

Dosimeters constructed according to the present invention and as tested according to the above procedures have been found to accurately reflect $NO_2$ in concentrations up to about 10 parts per million on a time-weighed integrated basis. The time periods for testing can be up to at least about 6 or 8 hours. The accurate determination of $NO_2$ concentrations above about 10 parts per million on an instant basis is somewhat unnecessary since at these concentrations, $NO_2$ produces a noticeable and distinct odor. Accurate determinations of NO concentrations on a time-weighed integrated basis have been found to be accurate by the use of the present invention up to about 25 parts per million even in the presence of $NO_2$ in concentrations up to about 10 parts per million on a time-weighed integrated basis. A minimum concentration by which the method of the present invention is accurate would be on the order of about 2 parts per million of total $NO_x$.

The following specific examples are illustrative but not limitative of the invention, it being understood that similar results are obtainable with other combinations of conditions other than those specifically considered in the examples. All such variations which do not depart from the basic concept of the invention disclosed above are intended to come within the scope the appended claims.

EXAMPLE 1

Twenty dosimeters were prepared as shown in FIG. 1, each containing ~4 milliliters of an aqueous absorbing solution which was 0.0005 molar in sulfuric acid and 0.004 molar in hydrogen peroxide. The membrane utilized was an unbacked dimethyl silicone membrane approximately 1 mil in thickness.

After standardization of an Orion 92–07 nitrate ion electrode by the testing of various solutions containing known concentrations of $NO_3^-$ ion, a test chart was prepared whereby millivolt readings were plotted on a linear ordinate scale versus parts per million of $NO_3^-$ ion on a logarithmic scale at the abscissa. Thus, concentrations of $NO_3^-$ ion in the exposed dosimeters was obtained by determination of the millivolt readings of the solution and reference to the test chart to determine the corresponding $NO_3^-$ ion concentration level.

Sets of five dosimeters were each tested in the apparatus shown in FIG. 2 over a six-hour period. However, other results indicate that the response is directly proportional to exposure time and, therefore, the results obtained are significantly accurate for an eight-hour work day which would be expected in the field.

The $NO_3^-$ ion concentrations resulting from exposures of batches of five dosimeters for six hours to $NO_2$ gas are shown in Table I. The precision of the $NO_2$ analyses can be obtained by linear regression according to methods set forth in "Statistics Manual" by Crow et al., Dover Publications, New York (1960) or in "Statistics" by Freund, Prentice-Hall, Englewood Cliffs, N.J. (1970).

Table I

| $NO_a$ $(V/V)^a$, PPM | Nitrate Ion Concentrations Resulting From Varying Ambient $NO_2$ Levels $NO_3^-(W/V)^b$, PPM | Ratio $NO_3^-/NO_2$ Mean | Grand Mean |
|---|---|---|---|
| 3.7 | 5.2, 5.3, 4.6, 5.8, 5.3 | 1.42 | 1.44 |
| 3.7 | 4.4, 4.4, 5.1, 5.1, 4.7 | 1.28 | |
| 7.3 | 10.8, 11.8, 10.0, 10.0, 10.0 | 1.44 | |
| 8.0 | 12.6, 12.6, 14.3, 12.0, 12.3 | 1.60 | |

$^a$Refers to gas volume ratios (volume of $NO_2$ per million volumes of air).
$^b$Refers to weight-liquid volume ratios ($\mu$g $NO_3^-$/ml of solution).

As indicated above, the precision of the $NO_2$ analyses can be obtained by linear regression and the following results were obtained.

| | | |
|---|---|---|
| Correlation coefficient, r | = | 0.973 |
| Slope, y/x | = | 1.57 |
| Intercept on y axis | = | −0.622 |
| Standard error of estimate, $^sy/x$ | = | 0.89 ppm |

The standard error of estimate, $^sy/x$ is a measure of precision of the $NO_3^-$ values when the dosimeter is exposed to accurately known $NO_2$ gas concentrations. The standard error of estimate of $NO_2$ levels in unknown samples from the slope (1.57) of the regression can be calculated, i.e. $Sx/y = 0.89/1.57 = \pm 0.57$ ppm. These results indicate a good standard of precision.

The precision found in this experiment was such that similar dosimeters prepared under standard laboratory conditions with the concentrations of the reagents mentioned above in the aqueous absorbing solution could be exposed and use could be made of the 1.44 grand mean ratio without further determination of a new grand mean. Therefore, dosimeters prepared within standard laboratory conditions to duplicate the above dosimeters would be prepared, exposed to $NO_2$ and the millivolt reading utilizing the nitrate ion electrode would then be determined. From a standard test curve which had been recently prepared, the millivolt reading would be correlated to a level of $NO_3^-$ ion. When the level of $NO_3^-$ ion would be divided by 1.44, an integrated time-weighed exposure to $NO_2$ would be obtained.

It should be noted that caution should be exercised when using any dosimeter to determine integrated values of exposure to compounds having a C value. Such devices will not indicate an excursion concentration existing during a limited time.

EXAMPLE II

Dosimeters similar to those utilized in Example I were provided with an oxidation filter made by impregnating 7-centimeter glass-fiber filters (No. 934-AH from Reeve Angel) with acidic sodium dichromate prepared by dissolving 2.5 grams of sodium dichromate in 100 milliliters of a 2.5% sulfuric acid aqueous solution. The thus-prepared oxidation filter was placed in the dosimeter shown in FIG. 1 between the top of the O-ring 2 and the cover ring 1.

Fourteen dosimeters in two groups of five each and one group of four were exposed to three different levels of NO gas as shown below in Table II. It should be noted that the levels of NO were not exactly maintained at the levels shown. Rather, the levels indicated in Table II represent time-weighed averages for exposures.

Table II

| Nitrate Ion Concentration Resulting From Chromate Oxidation Of Varying Ambient NO Levels To $NO_2$ | | |
|---|---|---|
| NO (V/V), PPM | $NO_3^-$ (W/V), PPM | Ratio (Mean) $NO_3^-$/NO |
| 2.8 | 3.8, 3.5, 3.0, 3.0, 3.2 | 1.18 |
| 7.0 | 10.0, 9.8, 9.8, 9.5, 8.9 | 1.38 |
| 10.3 | 14.5, 15.0, 14.5, 14.0 | 1.41 |

The ratio of $NO_3^-$/NO is significantly lower at low NO concentration, indicating that absorption efficiency is greater at higher concentrations of NO. A regression analysis, by the methods indicated in Example I, gave the following values:

| | | | |
|---|---|---|---|
| r | = | 0.997 | |
| slope | = | 1.50 | |
| intercept | = | −0.842 | |
| $S_{y/x}$ | = | 0.38 | ppm |

From the above, the standard error of estimate of NO levels in unknown samples can be calculated to show ± 0.25 ppm, which is a good level of precision.

In actual samples containing mixtures of $NO_2$ and NO, each component can be determined by simultaneous equations using the total $NO_3^-$ concentration found and the relative permeation rates, measured with and without the oxidation filter.

EXAMPLE III

Tests were conducted to determine the utilization of dosimeters prepared according to the present invention under various conditions. Firstly, dosimeter results for $NO_2$ exposure levels at several temperatures are summarized below in Table III.

Table III

| $NO_2$ Tests At Controlled Temperatures | | |
|---|---|---|
| Test Temperature °C | $NO_2$(V/V), PPM | $NO_3^-$/$NO_2$ (Mean for 5 Dosimeters) |
| 3.3 | 9.4 | 2.01 |
| 10.0 | 10.1 | 1.63 |
| 16.1 | 5.6 | 1.53 |
| 38.5 | 9.3 | 1.45 |

From the above, it can be seen that little change in the $NO_3^-$/$NO_2$ ratio occurs at temperature above about 15° C. Therefore, temperature corrections are unnecessary at normal ambient temperatures.

Secondly, in a similar set of experiments, it was found that the orientation of the dosimeter in various planes produced no difference in the levels of $NO_3^-$ ions produced.

Thirdly, the permeation of the aqueous absorbing solution through the membrane to the atmosphere was measured in various tests. Evaporation of the solution tends to increase at higher temperatures. However, these effects are essentially minimal at ambient temperatures during a six-hour test exposure. Thus, the liquid loss at about 16° C is about 5.3%.

While in the foregoing specification, embodiments of the invention have been described in detail, it will be appreciated that numerous changes may be made in those details by those skilled in the art without departing from the spirit and principles of the invention.

What we claim is:

1. A dosimeter for the detection of $NO_2$ gas comprising a container, open to the atmosphere only by means of a membrane which is substantially permeable only to gases, having therein an aqueous solution which converts $NO_2$ to $NO_3^-$ ion.

2. The dosimeter of claim 1, wherein said membrane is a dimethyl silicone membrane.

3. The dosimeter of claim 1, wherein said dosimeter holds about 2 to about 4 milliliters of said aqueous solution.

4. The dosimeter of claim 1, wherein said membrane is about 1 mil thick.

5. The dosimeter of claim 1, further comprising a means to attach said dosimeter to a wearer.

6. The dosimeter of claim 1, further comprising a converting means situated on the side of said membrane opposite from said aqueous solution for converting NO to $NO_2$ by which said dosimeter can detect levels of NO and $NO_2$.

7. The dosimeter of claim 6, wherein said converting means is a filter of an inert support material containing sodium dichromate.

8. The dosimeter of claim 1, wherein said aqueous solution comprises sulfuric acid, water and an oxidation agent which converts $NO_2$ to $NO_3^-$ ion.

9. The dosimeter of claim 8, wherein said oxidation agent is hydrogen peroxide.

10. The dosimeter of claim 8, wherein said aqueous solution is about 0.0005 molar in sulfuric acid and said oxidation agent is hydrogen peroxide present in an amount of about 0.004 molar.

11. A method for the determination of exposure to nitrogen dioxide gas in an atmosphere comprising the steps of:
  a. exposing to an atmosphere, a dosimeter comprising a container, open to the atmosphere by means of a membrane which is substantially permeable only to gases, having therein an aqueous solution which converts $NO_2$ to $NO_3^-$ ion;
  b. determining the concentration of $NO_3^-$ ion in solution; and
  c. determining the concentration of $NO_2$ in said atmosphere by correlation of said concentration of $NO_3^-$ with other concentrations of $NO_3^-$ ions found when said dosimeter was exposed to known concentrations of $NO_2$ gas.

12. The method of claim 11, wherein said aqeuous solution is present in said dosimeter in an amount of about 2 to about 4 milliliters.

13. The method of claim 11, wherein said exposing step (a) is performed by the wearing of said dosimeter by a worker in an atmosphere suspected of containing $NO_2$ gas.

14. The method of claim 11, wherein said aqueous solution is about 0.0005 molar in sulfuric acid and said oxidation agent is hydrogen peroxide present in an amount of about 0.004 molar.

15. The method of claim 11, wherein said exposing step (a) is performed at a temperature of from about 15° to 50° C.

16. The method of claim 11, wherein the concentration of $NO_2$ gas is said atmosphere is from about 1.2 to 10 parts per million.

17. The method of claim 11, wherein chloride ion is removed from said aqueous solution after step (a) and before (b).

18. The method of claim 17, wherein said chloride ion is removed by the precipitation of an insoluble chlorine compound.

19. The method of claim 18, wherein said insoluble chlorine compound is silver chloride.

20. A method for the determination of exposure to NO and $NO_2$ gases in an atmosphere comprising the steps of:
   a. exposing to an atmosphere, a dosimeter comprising a sealed container, open to the atmosphere by means of a membrane which is substantially permeable only to gases, having therein an aqueous solution which converts $NO_2$ to $NO_3^-$ ion and which contains a converting means, situated on the side of said membrane opposite from said aqueous solution, for converting NO to $NO_2$;
   b. determining the concentration of $NO_3^-$ ion in said solution; and
   c. determining the concentraton of NO and $NO_2$ in said atmosphere by correlation of said concentration of $NO_3^-$ with other concentrations of $NO_3^-$ ion found when said dosimeter was exposed to known concentrations of NO and $NO_2$.

21. The method of claim 20, wherein said aqueous solution is present in said dosimeter in an amount of from about 2 to about 4 milliliters.

22. The method of claim 20, wherein said exposing step (a) is performed by the wearing of said dosimeter by a worker in an atmosphere suspected of containing NO and $NO_2$ gases.

23. The method of claim 20, wherein said aqueous solution is about 0.0005 molar in sulfuric acid and said oxidation agent is hydroen peroxide present in an amount of about 0.004 molar.

24. The method of claim 20, wherein said exposing step (a) is performed at a temperature of from about 15° to 50° C.

25. The method of claim 20, wherein the concentration of $NO_2$ gas in said atmosphere is from about 1.2 to 10 parts per million and the concentration of said NO gas in said atmosphere is from about 2 to 25 parts per million.

26. The method of claim 20, wherein chloride ion is removed from said aqueous solution after step (a) and before step (b).

27. The method of claim 26, wherein said chloride ion is removed by the precipitation of an insoluble chlorine compound.

28. The method of claim 27, wherein said insoluble chlorine compound is silver chloride.

* * * * *